US009727961B2

(12) United States Patent
Wang et al.

(10) Patent No.: US 9,727,961 B2
(45) Date of Patent: Aug. 8, 2017

(54) METHOD OF OPERATING A RADIOGRAPHIC INSPECTION SYSTEM WITH A MODULAR CONVEYOR CHAIN

(71) Applicant: Mettler-Toledo Safeline X-Ray Ltd., Royston (GB)

(72) Inventors: Xinchi Wang, Barnet (GB); Nigel John King, Langford (GB)

(73) Assignee: METTLER-TOLEDO SAFELINE X-RAY LTD., Royston (GB)

( * ) Notice: Subject to any disclaimer, the term of this patent is extended or adjusted under 35 U.S.C. 154(b) by 586 days.

(21) Appl. No.: 14/310,010

(22) Filed: Jun. 20, 2014

(65) Prior Publication Data
US 2015/0003583 A1 Jan. 1, 2015

(30) Foreign Application Priority Data
Jun. 27, 2013 (EP) ..................................... 13174101

(51) Int. Cl.
*G01N 23/04* (2006.01)
*G06T 7/00* (2017.01)
(Continued)

(52) U.S. Cl.
CPC ........... *G06T 7/0004* (2013.01); *G01N 23/04* (2013.01); *G01T 7/005* (2013.01); *G01V 5/0016* (2013.01); *G06T 7/194* (2017.01); *G01N 2223/643* (2013.01); *G06T 2207/10116* (2013.01); *G06T 2207/10121* (2013.01); *G06T 2207/30128* (2013.01); *G06T 2207/30136* (2013.01)

(58) Field of Classification Search
CPC .. G01N 2223/643; G01N 23/04; G01T 7/005; G01V 5/0016; G06T 2207/10116; G06T 2207/10121; G06T 2207/30128; G06T 2207/30136; G06T 7/0004; G06T 7/194
See application file for complete search history.

(56) References Cited

U.S. PATENT DOCUMENTS

| 3,768,645 A | 10/1973 | Conway et al. |
| 2004/0247167 A1 | 12/2004 | Bueno et al. |

(Continued)

FOREIGN PATENT DOCUMENTS

| EP | 2711694 A1 | 3/2014 |
| JP | 2001-91480 A | 4/2001 |

(Continued)

*Primary Examiner* — Glen Kao
(74) *Attorney, Agent, or Firm* — Standley Law Group LLP

(57) ABSTRACT

A method of operating a radiographic inspection system is designed for a radiographic inspection system in which a conveyor chain with identical modular chain segments transports the articles being inspected. The method encompasses a calibration mode and an inspection mode of the radiographic inspection system. In the calibration mode, calibration data characterizing the radiographic inspection system with the empty conveyor chain are generated and stored as a template image. In the inspection mode, raw images (50) of the articles (3) under inspection with the background (41) of the conveyor chain are acquired and arithmetically merged with the template image. The method results in a clear output image (51) of the articles under inspection being obtained without the interfering background of the conveyor chain.

19 Claims, 5 Drawing Sheets

(51) Int. Cl.
*G01T 7/00* (2006.01)
*G01V 5/00* (2006.01)
*G06T 7/194* (2017.01)

(56) References Cited

U.S. PATENT DOCUMENTS

| | | |
|---|---|---|
| 2008/0166033 A1 | 7/2008 | Bueno et al. |
| 2010/0002835 A1 | 1/2010 | Kabumoto et al. |
| 2012/0128133 A1 | 5/2012 | King |
| 2013/0126299 A1* | 5/2013 | Schoepe .............. G01V 5/0083 198/340 |
| 2015/0192690 A1* | 7/2015 | Bridger ................ G01V 5/0016 378/57 |

FOREIGN PATENT DOCUMENTS

| | | |
|---|---|---|
| WO | 2009/030923 A1 | 3/2009 |
| WO | 2009/114928 A1 | 9/2009 |

* cited by examiner

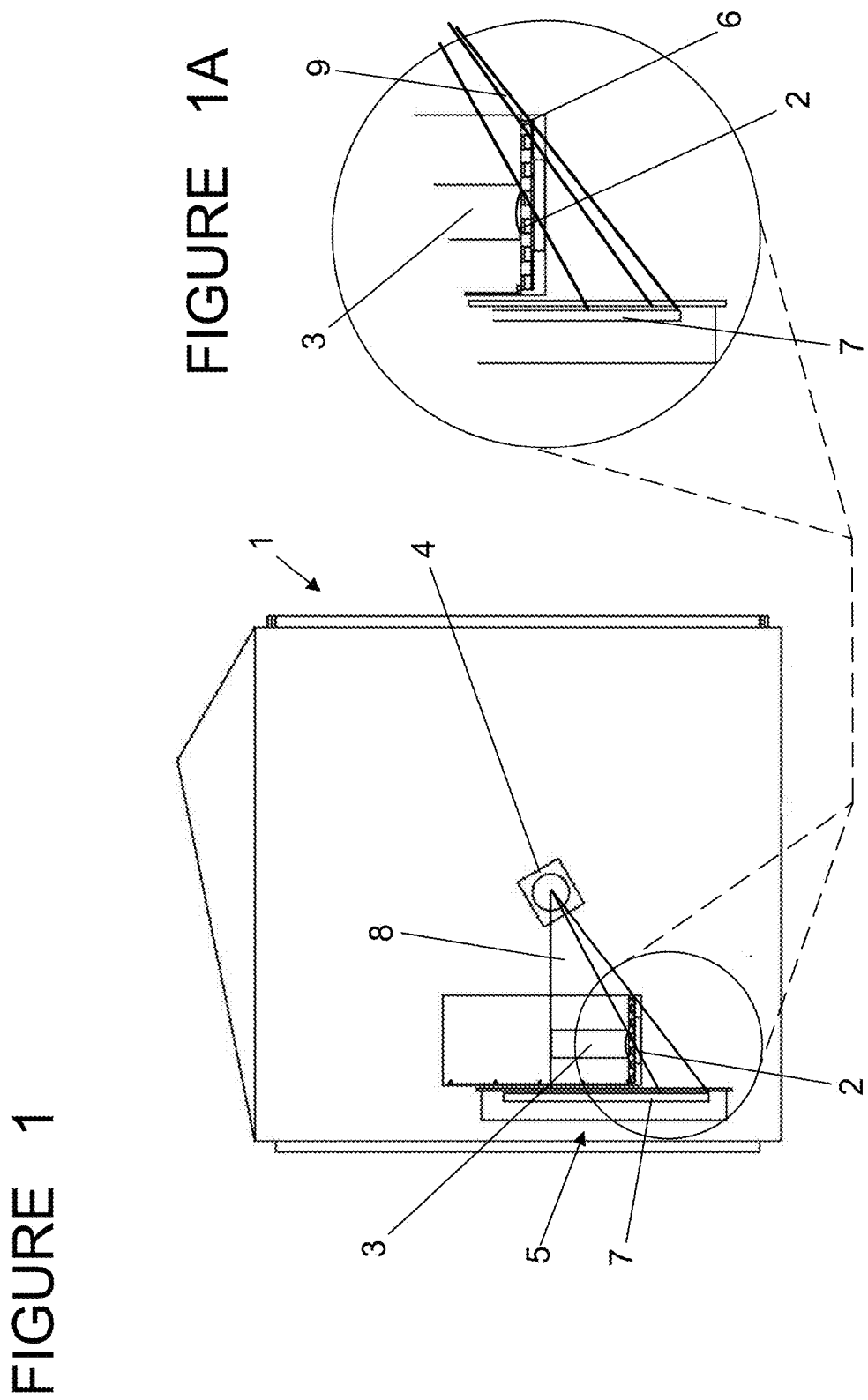

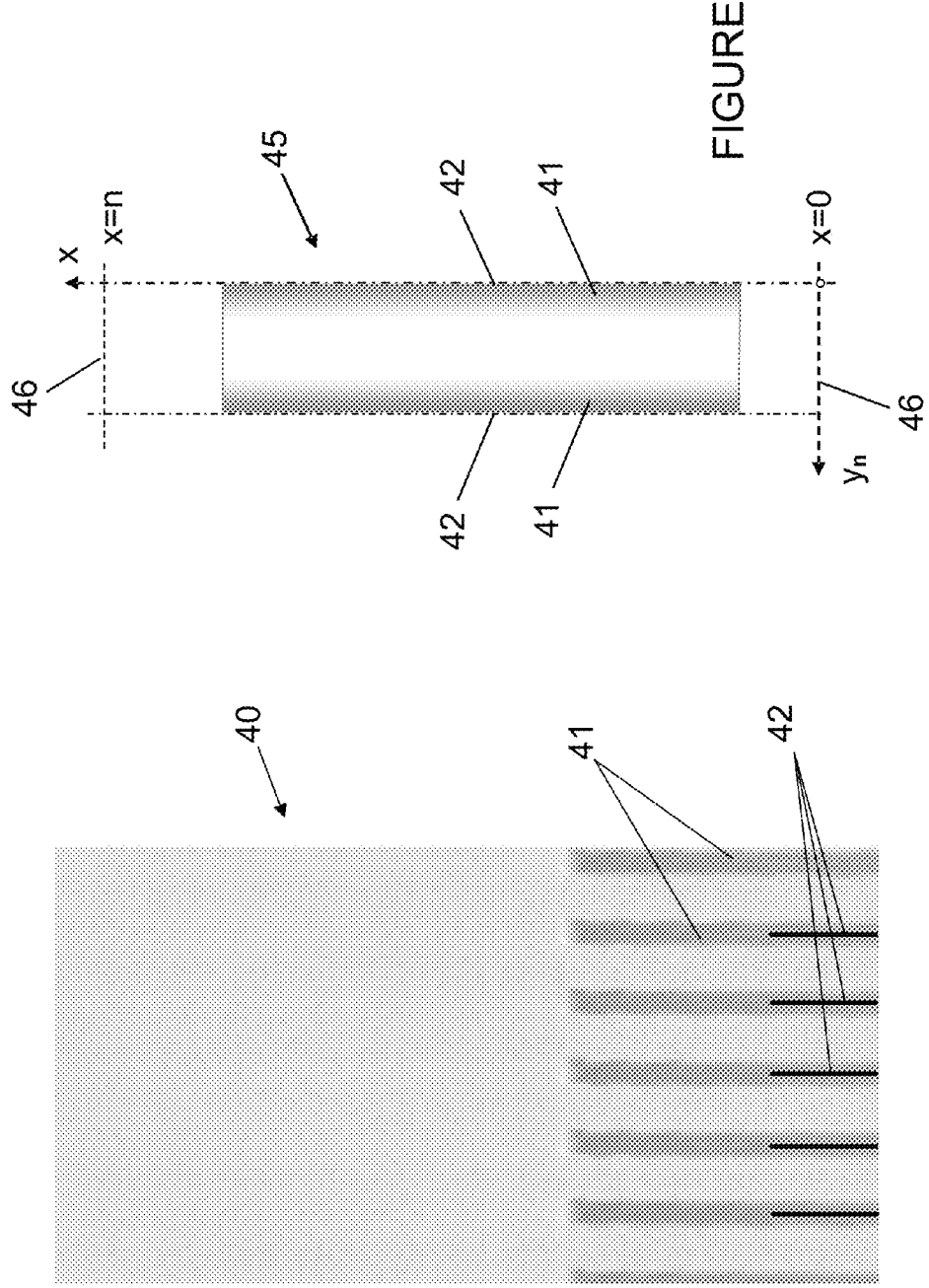

METHOD OF OPERATING A RADIOGRAPHIC INSPECTION SYSTEM WITH A MODULAR CONVEYOR CHAIN

CROSS-REFERENCE TO RELATED APPLICATIONS

This application claims a right of priority under 35 USC §119 from EP 13174101.9, filed on 27 Jun. 2013, which is incorporated by reference as if fully recited herein.

TECHNICAL FIELD

The invention relates to the field of radiographic inspection systems in which the articles under inspection travel on an endless-loop conveyor through an X-ray machine or other radiographic scanner system. In particular, the invention relates to a method of operating a radiographic inspection system in which the endless-loop conveyor is a modular conveyor chain, and the specific subject of the invention is a method of cancelling the effect that transmittance variations of the conveyor chain have on the radiographic image produced by the scanner system. In addition, the invention also concerns a radiographic inspection system with the requisite features to carry out the method.

BACKGROUND

The term "conveyor chain" in the present context means an endless-loop conveyor device analogous to a conveyor belt, but with the difference that a conveyor chain is comprised of a multitude of rigid segments or links which are connected to each other in a closed loop wherein each link is articulately hinged to a following link and a preceding link. The segments can either be all identical to each other, or a group of dissimilar segments can identically repeat itself around the conveyor chain. The individual segment or group of segments that identically repeats itself is referred to herein as a module or a modular segment and, consequently, the conveyor chain is referred to as a modular conveyor chain.

The radiation transmittance of the endless-loop conveyor comes into play in inspection systems whose geometric arrangement is such that at least part of the scanner radiation passes not only through the products under inspection and the air space surrounding them, but also traverses the endless-loop conveyor. This kind of inspection system is used for example for the detection of foreign bodies in bottled or canned food and beverage products. Of particular concern are metal and glass fragments in liquid products. Due to their higher density relative to the liquid, such foreign bodies will collect at the bottom of the container. Furthermore, if the container has a domed bottom, the foreign bodies will tend to settle at the perimeter where the bottom meets the sidewall of the container. It is therefore very important for the radiographic scanner system to be configured and arranged in relation to the endless-loop conveyor in such a way that the entire inside bottom surface of each container is covered by the scan. Consequently, it is necessary to use a scanner arrangement where at least part of the radiation passes through the bottom of the container and therefore also through the area of the endless-loop conveyor on which the container or any other object to be inspected is positioned.

In a typical arrangement, the rays used for the inspection may for example originate from a source located above and to the side of the conveyor path, enter the container at an oblique angle through the sidewall, exit through the container bottom and pass through the conveyor, to be received by a camera system which is connected to an image-processing system. Alternatively, for example if objects are inspected that are neither bottled nor canned, the radiation source can be arranged vertically above, and the radiation detector vertically below, the conveyor.

If the radiographic inspection system is an X-ray system, the rays can be received for example by an X-ray image intensifier and camera, or by an X-ray line array sensor which, in response, sends a signal to the image processing system. Typically, the imaging radiation originates as a fan-shaped planar bundle of rays from a localized source, i.e. a spot-sized radiation source and is received by a linear array of photodiodes that are collectively referred to as a detector, wherein the fan-shaped radiation bundle and the linear array of photodiodes lie in a common plane, also referred to as the scanning plane, which runs substantially orthogonal to the travel direction of the conveyor carrying the articles to be inspected. While the articles under inspection move through the scanning plane, the linear array of photodiodes is triggered by a continuous sequence of discrete pulses, and the pulse frequency is coordinated with the speed of the conveyor so that the sequence of signals received by the detector array can be translated into a pattern of raster dots with different brightness values expressed for example in terms of a brightness scale from zero to 255, representing a transparent shadow image of the material bodies between the radiation source and the radiation detector. If a scanned article contains foreign objects such as metal fragments, which have a lower transmittance to the scanning rays than the scanned article, the radiographic image will show such foreign objects as darker areas within the transparent shadow image of the scanned article.

At the present state of the art, endless-loop conveyors that are used as transport devices in radiographic inspection systems are in most cases polymer fabric belts. This type of conveyor has the advantage that the quality of the X-ray image is least affected by it, due to the constant thickness and the uniformity of the belt. However, there are a number of strong arguments against polymer fabric belts and in favor of modular conveyor chains, specifically:

- There is strong resistance to the use of fabric belts particularly in the bottling and canning industry, because they are easily damaged and wear out rapidly. In comparison, conveyor chains consisting of rigid plastic elements (typically of acetal resin or polypropylene) that are linked together in an endless loop are much stronger and less easily damaged by hard metal or glass containers.
- Conveyor chains are better suited for heavy-weight articles such as blocks of cheese, as it is possible to drive the conveyor chain with sprockets that directly engage the chain profile.
- The segments of a conveyor chain can be hinged together in such a way that the chain has a unilateral flexibility to loop around the drive sprockets while being rigid against bending in the opposite direction. This latter property eliminates the need for guiding mechanisms which can be unreliable in continuous-duty applications.
- Conveyor chains are easier to replace or repair than belts, because the chain can be opened by removing one of the hinge pins by which the modular segments of the chain are linked together.
- Conveyor chains can be designed to be self-tracking and to run flush with the sides of the conveyor support structure. This last characteristic is important, because it allows products to be easily transferred sideways between laterally adjacent conveyors.

Nevertheless, the use of customary chain conveyors with plastic chain links is problematic in radiographic inspection systems, because the chain links can interfere with the X-ray image. Until now, if one wished to X-ray a product moving on a conveyor chain, the resultant image was degraded by the variations in the transmittance of the conveyor chain superimposed on the product, for example due to hinges or other connections between the chain segments or by profile features designed to stiffen the chain segments. If this problem of image interference can be solved, the benefits of modular conveyor chains as listed above can be applied to radiographic inspection systems.

In US published application 2012/0128133 A1, which is owned by the same assignee as the present invention, the problem of transmittance variations is solved through a conveyor chain in which the chain segments are configured in essence as rigid plates of uniform thickness and density extending over the width of the conveyor chain, wherein the segments overlap each other to present themselves to the scanner radiation as a substantially gapless band of uniform transmittance and wherein the connectors or hinges which link the segments together (and which have a lower transmittance than the flat areas of the segments) are located outside the band that is traversed by the scanner radiation. Thus, the connections between the segments are preferably located in the two lateral border areas of the conveyor chain.

In a conveyor chain according to the foregoing concept, the absence of hinges or any other stiffening features in the central homogeneous band area reduces the rigidity of the chain segments in regard to transverse bending and therefore limits the conveyor width that can be realized in a practical design.

Another solution is offered in unpublished European patent application published as EP 2711694 A1 which is likewise owned by the assignee of the present invention and whose entire content is hereby incorporated by reference in the present disclosure. In short, a method of operating a radiographic inspection system is described which is specifically designed for a system in which a conveyor chain with identical modular chain segments is transporting the articles under inspection.

The method of European patent application EP 2711694 A1 encompasses two operating modes of the radiographic inspection system. In a first mode, referred to as calibration mode, an image of one modular segment of the empty conveyor chain is recorded and stored in the form of digital pixel data, referred to as calibration data. The reason why the calibration data are recorded only for one modular segment is that the set of calibration data repeats itself identically for each modular segment of the chain. In a second mode, referred to as inspection mode, an image of the articles under inspection with the background of the conveyor chain is recorded in the form of digital pixel data, referred to as raw image data. Immediately, i.e. after each row of pixels has been recorded, the raw image data are arithmetically processed into a clear output image by cancelling out the interfering background of the conveyor chain with the help of the calibration data.

In order to be able to geometrically correlate the raw image data collected in the inspection mode to the calibration data collected and stored in the calibration mode, every raster dot of the radiographic image needs to be registered in terms of x/y-coordinates relative to the modular segment, so that each pixel value can be stored together with its x/y address.

The registration coordinate x in the transverse direction of the modular segment (parallel to the hinge pin) can simply be based on the array position of the photodiode associated with that location within the radiographic image.

For the registration coordinate y in the longitudinal direction of the chain (i.e. the direction of conveyor movement) European patent application EP 2711694 A1 proposes the concept of a physical registration feature that is either part of the chain or moves together with the chain. In a preferred embodiment, the registration feature is realized as a ramp-shaped lateral border portion formed on the modular segment. In operation, the ramp-shaped border intercepts a marginal sector of the fan-shaped radiation bundle, so that the image received by the sensor array will be representative of the ramp height, from which the longitudinal registration coordinate y can be directly calculated by the processor.

In the foregoing method and apparatus according to European patent application EP 2711694 A1, the physical registration feature as exemplified by the ramp is a feature that is not normally present in a conveyor chain and is added for the sole purpose of providing a registration reference in the longitudinal direction y of the conveyor chain. It occurred to the inventors that, as an alternative to adding a physical feature to the conveyor chain, the raw image data collected in the inspection mode could also be geometrically correlated to the calibration data by using known techniques of image-matching and image interpolation to register an inspection image directly against the stored background image without the help of a specifically dedicated physical registration feature.

In view of the strong potential seen in the techniques of image matching and interpolation as a solution to the problem of accurately registering an inspection image against a calibration image in the process of radiographic product inspection, the present invention has the objective to provide a viable alternative to the use of a specifically dedicated physical registration feature for geometrically matching the raw images of inspected articles to the background image of the modular conveyor chain.

SUMMARY

The stated objective of the invention is met by a method of calibrating and operating a radiographic inspection system in accordance with independent claim 1 and by a radiographic inspection system having the requisite capabilities as set forth in claim 13. Detail features and further developed traits of the invention are defined in the dependent claims.

The method according to the invention is designed for use in a radiographic inspection system with a radiation source emitting scanning rays, further with a radiation detector receiving the scanning rays and converting them into detector signals, with a processor generating a radiographic image based on the detector signals, and with a modular conveyor chain with identical modular segments that are connected in a closed loop, wherein articles under inspection are transported on the modular conveyor chain through a space that is traversed by the scanning rays. In accordance with the invention, the method accomplishes the task of removing from said radiographic image a background image that is caused essentially by the conveyor chain segments and by factors inherent in the radiation detector. As a result, an output image is obtained which shows the articles under inspection without the interfering background image of the conveyor chain.

In essence, the method encompasses two operating modes of the radiographic inspection system, i.e. a calibration mode and an inspection mode.

In the calibration mode, data reflecting the influence of the radiation source and the radiation detector as well as image data for at least one of the modular segments are acquired by the radiographic inspection system and digitally processed into calibration data which are then stored as a template image in a memory of the radiographic inspection system. The template image could be based on any single one of the modular segments, selected at random. However, to allow for manufacturing tolerances and, accordingly, for slight variations that may exist between the segments, it may be desirable to sample multiple segments and average the data. Thus, the template may represent a composite of a plurality of modular segments or even all of the modular segments of the conveyor chain.

In a first step C1) of the calibration mode, the dark signals of the individual photodiodes of the detector array are determined by measuring their respective diode currents while the radiation source is turned off. The respective "dark currents" of each diode are stored in memory as dark-level values. Subsequently, for every brightness value acquired in steps C2) and I1) by any of the photodiodes, the respective stored dark-level value for that diode will be subtracted from the measured diode current, so that the resultant net current value will be zero for all diodes if the radiation source is turned off.

In a second step C2) of the calibration mode, raw segment image data are acquired for one of the modular segments including adjacent border portions of the immediately preceding and the next following modular segment. The raw segment image data are retained in a data array as a raw segment image of the modular segment including adjacent border portions of neighboring modular segments.

In a third step C3) of the calibration mode, the data retained in step C2) are digitally processed into a normalized template image which is referenced to at least one clearly definable feature that occurs identically in the radiographic image of each of the modular segments. The normalized template image is stored as a digital data array in a memory file of the processor.

In the inspection mode, radiographic images of the articles under inspection with the background of the conveyor chain are acquired by the radiographic inspection system in the form of raw digital image data. The raw image data are arithmetically processed with the help of the previously stored template image data into clear output images of the articles alone without the interfering background of the conveyor chain.

In a first step I1) of the inspection mode, a raw radiographic image is acquired, one article at a time and including all conveyor chain segments which in the radiographic image are at least partially overlapped by the article. The raw radiographic image is retained in a two-dimensional data array.

In a second step I2) of the inspection mode, the raw digital image is arithmetically processed into a normalized digital image which is referenced to the at least one clearly definable feature, so that the normalized digital image and the normalized template image are congruently referenced against the least one clearly definable feature.

In a third step I3) of the inspection mode, the normalized digital image and the normalized template image are merged in an arithmetic procedure that removes the background of the conveyor chain from the normalized digital image by applying to the latter a correction corresponding to the normalized template image.

Each of the steps C1), C2), C3), I1), I2), I3) will be explained hereinafter in further detail after the requisite concepts and terminology will have been covered.

The method takes advantage of the fact that the conveyor chain is constituted by an endless loop of identical modular segments. Therefore, it is sufficient in the calibration mode to acquire, process and store the data for any single one of the modular segments rather than to acquire the data for an entire chain with typically several hundred segments, which would take a commensurately greater amount of time for the calibration mode and require a prohibitive amount of memory capacity to store the template image data.

The method according to the invention is preferably performed with a radiographic inspection system that has a radiation source of a spatially concentrated configuration, i.e. a localized or spot-sized radiation source and a radiation detector in the form of a linear array of photodiodes arranged at regular intervals, wherein the radiation source and the radiation detector face each other across the modular conveyor chain, wherein the scanning rays emanate as a fan-shaped planar bundle from the radiation source to the radiation detector and wherein the fan-shaped radiation bundle and the linear array of photodiodes lie in a common scanning plane which runs substantially orthogonal to the travel direction of the conveyor chain.

Further in a radiographic inspection system that is operable to perform the method of the invention, scanner radiation is generated by the radiation source in a continuous stream of radiation at least during time periods when an article is moving through the scanning plane, while during the same times the radiation detector is triggered by pulses to generate detector signals, wherein the timing of the pulses is synchronized with the movement of the conveyor chain so that the points in time when the fan-shaped planar bundle of radiation is producing an output signal of the radiation detector correspond to uniform travel intervals of the conveyor chain. Such pulses can be typically generated by a rotary or linear encoder.

At each individual trigger pulse, the radiation received by the individual photodiodes of the detector array is converted into a line of substantially equidistant image dots. As the trigger pulses are synchronized with the movement of the conveyor chain, any series of successive trigger pulses will produce a series of substantially equidistant parallel lines of image dots, so that the result will be a raster of lines and columns of image dots, wherein each line of image dots is associated with a trigger pulse occurring at a given point of the travel movement of the conveyor chain, and each column of image dots is associated with a specific photodiode in the linear array of photodiodes. Each image dot in the raster can be referenced by a raster coordinate x in terms of raster intervals in the direction perpendicular to the travel direction of the conveyor chain, and by a raster coordinate y in terms of raster intervals in the travel direction of the conveyor chain, wherein an origin of the x/y-coordinate system can be placed at an arbitrarily selected intersection of a raster line and a raster column, for example by assigning x=0 to the raster column associated with the photodiode at one end of the photodiode array, and assigning y=0 to the first raster line recorded for a finite time period during which an article is moving through the scanning plane. Each image dot in the raster is individually characterized by a level of brightness which can be expressed in digital form as a brightness value B(x,y), so that the totality of all brightness values B(x,y) can be processed and stored as a two-dimensional data array.

A brightness value B(x,y) of an image dot at a position (x,y) of the raster is determined by the following factors:

1. an individually different dark signal and light sensitivity of each photodiode in the detector array;
2. an individually different distance of each photodiode from the source of the fan-shaped radiation bundle;
3. an individually different amount of radiation intensity lost along a ray path from the radiation source to each photodiode due to absorption in the conveyor chain; and
4. an individually different amount of radiation intensity lost along the ray path from the radiation source to each photodiode due to absorption in an article under inspection.

Thus, the method according to the invention could be said to perform the task of cancelling the first three of the four determinant factors in a raw, i.e. untreated radiographic image, so that the resultant processed image represents only the amounts of radiation that were actually absorbed in the article under inspection.

In preferred embodiments of the invention, each modular segment has a substantially flat and relatively thin area with high and substantially uniform transmissibility to the radiation. This flat area is of substantially rectangular shape, extending in the x-direction over the entire width of the conveyor chain and extending in the y-direction from one hinge to the next. In the radiographic image, the flat areas of the modular segments appear as light areas, while the aforementioned clearly definable feature that occurs identically in the radiographic image of each of the modular segments consists of a dark stripe which represents the image of a hinge, so that in any radiographic image taken during operation of the radiographic inspection system the succession of modular segments forms a pattern of light and dark parallel stripes running transverse to the travel direction of the conveyor chain.

For such an embodiment of the invention, where the flat portions and the hinges of the modular segments produce a radiographic image of light and dark parallel stripes, the steps C1), C2), C3), I1), I2), I3) of the method according to the invention can now be defined more specifically as follows:

Step C1) of the calibration mode entails the operations:
turning off the radiation source,
measuring a diode current for each photodiode of the linear array of photodiodes, and
digitizing the diode current and storing it in a one-dimensional memory array as the dark signal D(x) for the diode at the array position x.

Next in the calibration mode follows step C2) with these operations:
turning the radiation source on and setting the conveyor chain in motion,
acquiring raw segment image data covering one of the modular segments including the full extent of the two dark stripes representing the hinges connecting the modular segment to the immediately preceding and the next following modular segment, and collecting the raw segment image data in a two-dimensional data array RSI(x,y), wherein an origin of the x/y-coordinate system can be defined for example by assigning x=0 to the raster column associated with the photodiode at one end of the photodiode array, and assigning y=0 to the first line of raster dots recorded in the acquisition of the raw segment image data.

Step C3) of the calibration mode entails a series of arithmetic operations, i.e.:
subtracting the dark signal D(x) from the raw segment image value RSI(x,y) to obtain a net segment image value NSI(x,y) for each x/y-location;
in the data array NSI(x,y) identifying the portions representing the dark stripes;
identifying a light area between the dark stripes and calculating a linear calibration array L(x) by averaging the net segment image values NSI(x,y) for each x-location within said light area;
calculating a gain factor $G(x)=k/L(x)$ for each photodiode position x, wherein k is a normalization factor (e.g. k=255 in case of 8 bit data);
multiplying every net segment image value NSI(x,y) with the gain factor G(x) for the respective x-position to obtain normalized segment image values $NOS(x,y)=G(x) \times NSI(x,y)$;
based on the normalized segment image values NOS(x,y), calculating within each of the two dark stripes an image-intensity-weighted centroid line within a fraction of a raster interval in the y-direction;
transforming the normalized segment image values NOS(x,y) into normalized calibration template values $NCT(x,y_n)$ referenced to a normalized coordinate raster $(x,y_n)$ wherein the coordinate $y_n$ originates from the centroid line and is scaled in terms of the periodic interval (or a fraction thereof) between two centroid lines, and wherein the brightness value assigned to each normalized calibration template value $NCT(x,y_n)$ is obtained by interpolation between adjacent normalized segment image values NOS(x,y); and
storing the normalized calibration template values in a memory array $NCT(x,y_n)$ as the digital template image.

The normalized coordinate raster $(x,y_n)$ is a fundamental aspect of the present invention, in that it provides the frame for the template image as well as the means of registration for each raster dot within the template image. The frame is formed by the two centroid lines representing the hinges to the neighboring modular segments, and by the two border columns of raster dots representing, respectively, the first and the last diode of the detector array. As the fan-shaped planar bundle of radiation extends outside the width of the conveyor chain on both sides of the latter, the origin x=0 and the endpoint x=n (wherein n+1 is the number of photodiodes in the detector array) of the x-coordinate of the template lie on opposite sides outside the width of the conveyor chain. In other words, the template image represents not only the modular segment of the conveyor chain but also the additional widths of air space on both sides of the conveyor chain which are traversed by the imaging rays. The raster interval as well as the origin of the $y_n$-axis can be arbitrarily selected, for example by defining the $y_n$-scale interval as 1/100 of the interval between the centroid lines forming the template frame and assigning $y_n=0$ to the centroid line representing the first hinge that passed through the scanning plane and $y_n=100$ to the opposite border of the template frame, which represents at the same time the template coordinate $y_n=0$ for the next modular segment.

In the normal operating mode, referred to herein as inspection mode, the following steps are performed in direct succession for each article passing through the scanning plane:

Step I1) includes these operations:
sensing the approach of an article to the scanning plane; and acquiring a raw radiographic image of the article including the total extent of all conveyor chain segments which in the radiographic image are at least partially overlapped by the article, and retaining the raw image data in the form of a data array RID(x,y) of raw brightness values, wherein the x/y-coordinate system can be defined in a manner analogous to step C2).

Step I2) of the inspection mode includes the operations:
subtracting the dark signals D(x) from the raw image data RID(x,y) to produce net image data NID(x,y);
multiplying every net image value NID(x,y) with the gain factor G(x) for the respective x-position to obtain normalized image values NOI(x,y)=G(x)×NID(x,y);
in the data array NOI(x,y) identifying the portions representing the dark stripes and applying the image-intensity-weighted centroid line calculation to those parts of the dark stripes which are not overlapped by the image of an article under inspection;
transforming the data array NOI(x,y) into a template-referenced image array $TRI(x,y_n)$ which is referenced to the coordinate raster $(x,y_n)$ of the template image representing, e.g., the first full modular segment in the underlying background, wherein the brightness value assigned to each raster dot in the template-referenced image array $TRI(x,y_n)$ is obtained by interpolation between adjacent normalized image data values NOI (x,y).

Step I3) of the inspection mode includes the operations:
merging the template-referenced image array $TRI(x,y_n)$ and the normalized calibration template array $NCT(x,y_n)$ in an arithmetic procedure that removes the background of the hinges from the template-referenced digital image, wherein for each raster location $(x,y_n)$ the respective pixel value $TRI(x,y_n)$ is individually corrected based on the corresponding value $NCT(x,y_n)$ of the calibration template array, resulting in a final radiographic image of the article without the background of the modular conveyor chain;
analyzing the final radiographic image for the presence of irregularities such as foreign objects that may be contained in the article.

The scope of the present invention also encompasses a radiographic inspection system with the requisite features and capabilities to perform the method in accordance with any of the aspects covered in the foregoing description. In particular, the radiographic inspection system according to the invention is equipped on the one hand with a modular conveyor chain with identical modular segments wherein each of the identical modular segments comprises at least one element which will present itself as a prominent and clearly defined image feature in the radiographic image, and on the other hand with a processor capable of establishing a normalized template raster and template image of the modular segment based on the prominent and clearly defined image feature, and applying the template to the task of removing the background of the conveyor chain from the image of an article under inspection.

In a preferred embodiment of the radiographic inspection system, the at least one prominent and clearly defined image feature consists of parallel and equidistant dark stripes in the radiographic image of the modular conveyor chain, wherein the dark stripes represent the hinges that connect each modular chain segment to a preceding and a next-following segment in the endless loop of the conveyor chain.

It is further preferred, if each modular segment has a substantially flat and relatively thin area with high and substantially uniform transmissibility to the radiation. This flat area is of substantially rectangular shape, extending in the x-direction over the entire width of the conveyor chain and extending in the y-direction from one hinge to the next. In the radiographic image, the flat areas of the modular segments appear as light areas, so that the succession of modular segments forms a pattern of light and dark parallel stripes running transverse to the travel direction of the conveyor chain in any untreated radiographic image taken during operation of the radiographic inspection system.

In preferred embodiments of the radiographic inspection system, the radiation consists of X-rays because of their ability to penetrate objects that are impermeable to visible light. Since the photodiodes of the detector array have a spectral sensitivity that is greatest for light with a longer wavelength than X-rays, they preferably carry a fluorescent coating designed to convert the X-rays into light of a wavelength matched to the spectral sensitivity of the photodiodes.

BRIEF DESCRIPTION OF THE DRAWINGS

The following description of specific embodiments and details of the invention is supported by the attached drawings, wherein FIG. 1 illustrates a radiographic inspection system with the requisite features to implement the method, with FIG. 1A representing an enlarged detail of FIG. 1;

FIG. 4A represents the radiographic image of an empty conveyor chain, wherein the equidistant dark stripes represent hinges and the thin straight lines in the dark stripes represent centroid lines;

FIG. 4B represents a normalized template image derived from the radiographic image of FIG. 4A, including the template frame and the template raster;

DETAILED DESCRIPTION OF SPECIFIC EMBODIMENTS

Figure 2A:
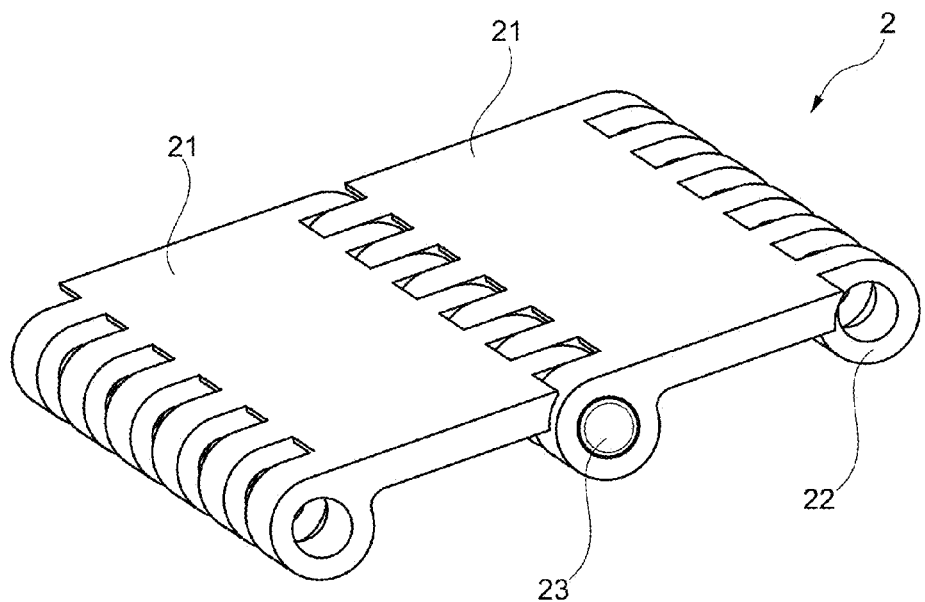
FIGS. 2A, 2B, 2C represent different views of a part of the conveyor chain in a radiographic inspection system according to the invention.

FIGS. 1 and 1A illustrate a radiographic inspection system 1 of a suitable configuration to carry out the method according to the invention. The principle elements of the radiographic inspection system 1 are the modular conveyor chain 2 (shown in cross-section with its transport direction oriented towards the viewer), an article 3 being transported on the conveyor chain 2, a radiation source 4, and a detector 5 with a linear photodiode array 7. The radiation source 4 is spot-sized, preferably extending over an area of about 1 mm$^2$ and generates imaging rays which emanate as a fan-shaped planar bundle from the radiation source 4 to the photodiode array 7 of the detector 5. A segment 8 of the fan of imaging rays passes through the article 3, and a segment 9 of the imaging rays passes only through the conveyor chain 2 without traversing the article 3. The signals produced by the photodiodes in the array 7 in response to one trigger pulse are converted by a computer or processor (not shown in the drawing) of the radiographic inspection system 1 into a line of image dots of a raster-shaped radiographic image representing the modular conveyor chain 2 and the articles 3 being transported on it. As the conveyor chain 2 with the articles 3 is continuously moving, each trigger pulse—such pulses as are typically generated by a rotary or linear encoder—received by the radiation detector 5 produces a new line of the raster-shaped radiographic image.

Figure 2B:
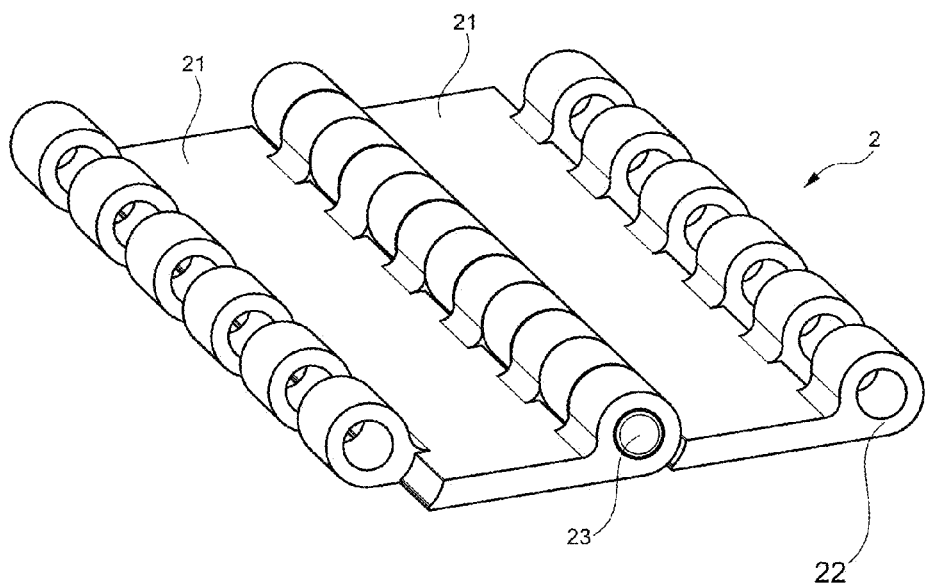
Figure 2C:
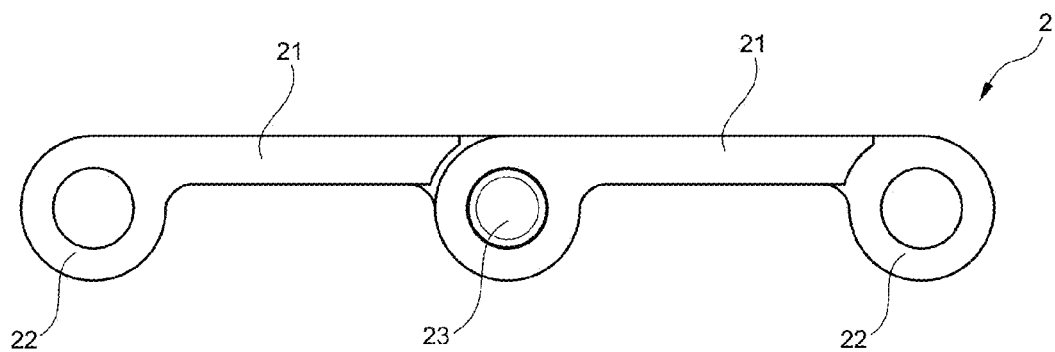

FIG. 2A shows two segments 21 of the modular conveyor chain 2 in a perspective view directed at the transport surface of the conveyor chain, while FIG. 2B represents a perspective view directed at the underside and FIG. 2C represents a side view of the conveyor chain segments 21. The segments 21 are connected to each other by hinges 22 with hinge pins 23 which extend over the entire width of the conveyor chain 2. While the hinges 22 and hinge pins 23 should be transparent to the imaging radiation of the inspection system, they should nevertheless be of sufficient optical density to present themselves as dark stripes whose brightness-weighted centroid lines (see FIG. 4A) can be reliably determined.

Figure 3:
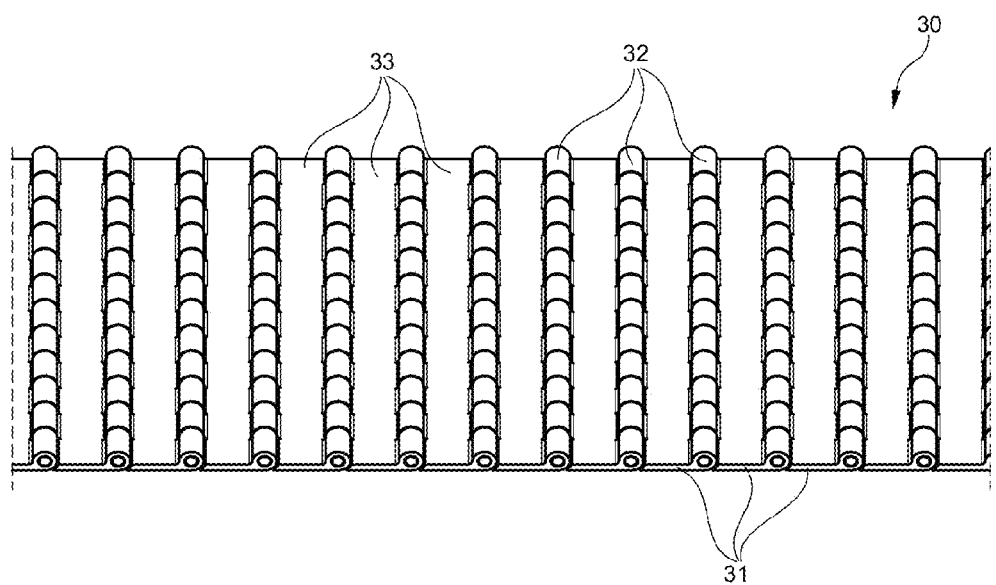
FIG. 3 represents a modular conveyor chain of the kind used in a preferred embodiment of the invention.

FIG. 3 represents a modular conveyor chain 30 of the kind used in a preferred embodiment of the invention. The view is directed at the underside of the conveyor chain 30, from which the contours of the hinges 32 protrude as pronounced ridges, in contrast to the topside or transport side of the conveyor chain 30, which is a flat surface. Except for the hinges 32 the modular segments 31 are flat and of a uniform, low thickness.

FIG. 4A represents a radiographic image 40 of the empty conveyor chain 30 of FIG. 3 as it would appear for example in the inspection system 1 of FIG. 1 after the normalization procedures of the calibration mode. In the normalized image NOS(x,y), the flat areas 33 of the conveyor chain segments 31 have the same image intensity level, for example of 255, as the adjacent air space that is traversed by a part of the scanning radiation, which means that the calibration has canceled out the radiographic effect of the flat parts of the conveyor segments. The more massive hinge portions 32 of the segments 31 of the conveyor chain 30 appear as dark parallel stripes 41. The location of the centerlines 42 of these dark stripes 41 in relation to a raster of the raw uncalibrated image has been determined by a brightness-weighted centroid calculation which provides a sub-pixel level of accuracy.

FIG. 4B illustrates how a template image 45 can be defined in the normalization procedure of the calibration mode. The template image 45 is delimited by a template frame which is formed by the two centerlines 42 representing the hinges 32 connecting the modular segment 31 to the neighboring modular segments, and by the two border columns 46 of raster dots representing, respectively, the first and the last diode of the detector array. As the fan-shaped planar bundle of radiation extends outside the width of the conveyor chain on both sides of the latter, the origin x=0 and the endpoint x=n (wherein n+1 is the number of photodiodes in the detector array) of the x-coordinate of the template lie on opposite sides outside the width of the conveyor chain. In other words, the template image represents not only the modular segment of the conveyor chains but also the additional widths of air space on both sides of the conveyor chain which are also traversed by the imaging rays. The raster interval on the $y_n$-axis can be arbitrarily selected, for example as 1/100 of the interval between the centerlines 42 forming the template frame, setting for example $y_n$=0 for the centerline of the first hinge recorded in the scan and $y_n$=100 for the opposite border of the template frame, which represents at the same time the template coordinate $y_n$=0 for the next modular segment 31.

Figure 5A:
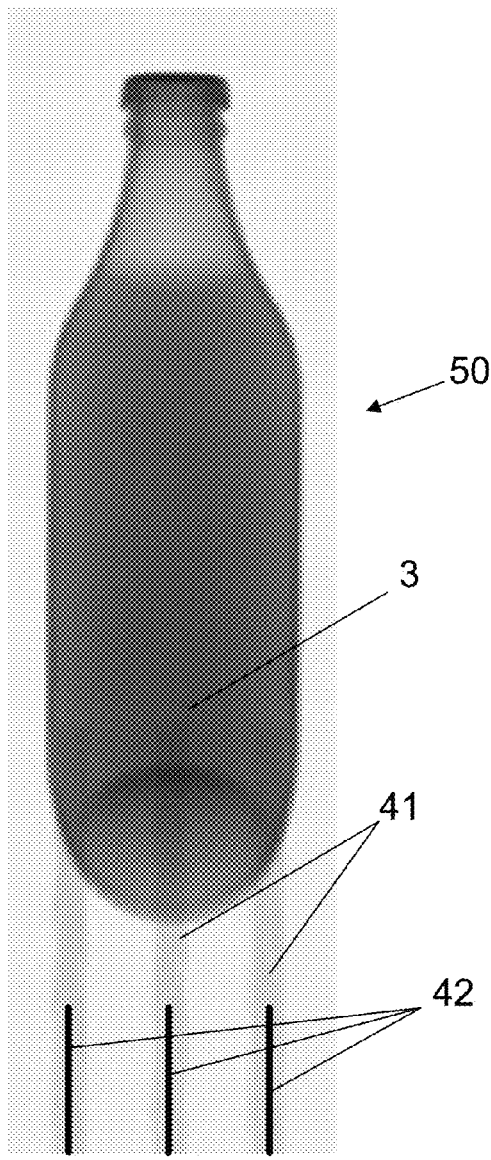
FIG. 5A shows an untreated radiographic image of an inspected article, including the background of dark stripes.

FIG. 5A shows an intermediate radiographic image 50 of an inspected article, wherein the centerlines 42 of the dark stripes 41 have been determined and the normalized raster coordinate system has been established, so that the background can be registered to the template image, or in this case a composite of three complete template images that are joined together to represent the background in this image of the article.

Figure 5B:
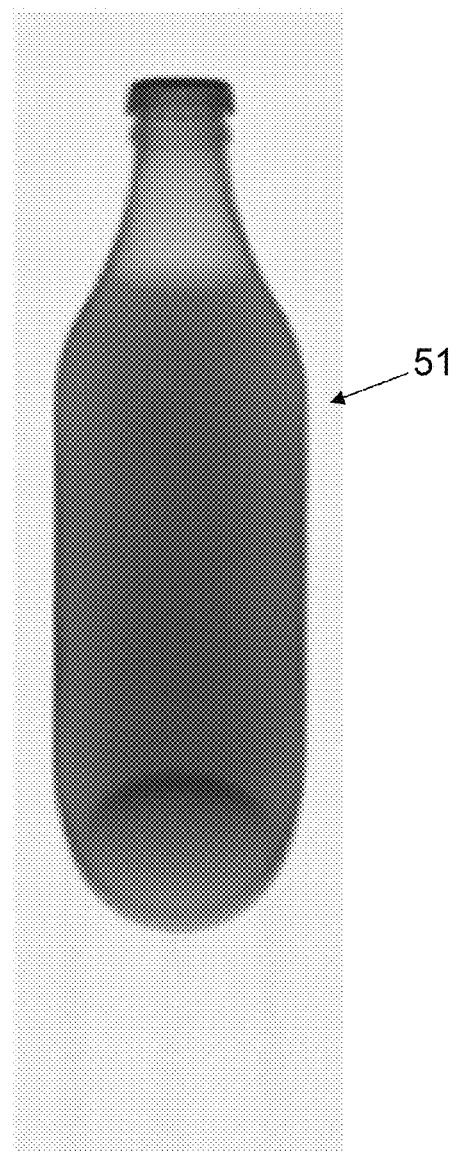
FIG. 5B shows the image of FIG. 5A after the background has been removed through the method according to the invention.

FIG. 5B shows the result of the method according to the invention: the final radiographic image 51 of the article 3 of FIG. 5A after the background stripes 41 have been removed.

Although the invention has been described through the presentation of specific examples of embodiments, it will be evident to the reader that numerous further variant embodiments could be developed from the teachings of the present invention, for example by combining the features of the individual examples with each other and/or by interchanging individual functional units between the embodiments described herein. For example the inventive concept is applicable to radiation of any wavelength that can penetrate an object under inspection as well as the conveyor chain. A radiation detector other than a linear photodiode array can be used, such as a 2D-format radiation detector, for example an area photodiode array, an image intensifier, a flat panel imaging plate or a scintillation screen in combination with a camera, as well as other conceivable solutions for recording an image, wherein the inventive method of cancelling the background of a conveyor device from the radiographic image remains fully applicable. It goes without saying that any such variant embodiments are considered to be included in the scope of the present invention.

What is claimed is:

1. A method for operating a system for radiographic inspection of articles, the method comprising the steps of:
transporting, in a travel direction, an article being inspected on a modular conveyor chain that comprises a plurality of identical modular segments that are joined together by hinges to form a closed loop chain;
emitting scanning rays from a radiation source, the radiation source arranged so that the scanning rays traverse both the article and at least a portion of the modular conveyor chain;
receiving the scanning rays in a radiation detector comprising a plurality of photodiodes;
converting the received scanning rays in the radiation detector into detector signals; and
generating, from the detector signals, a generated radiographic image in a processor, the processor programmed to eliminate, in the generated radiographic image, a background image that is caused essentially by the conveyor chain segments and by factors inherent in the radiation detector, through the use of a calibration mode and an inspection mode,
wherein the calibration mode comprises the steps of:
measuring a diode current of each of the plurality of photodiodes while the radiation source is turned off and storing the measured diode currents as digital calibration data in a one-dimensional data array,
acquiring raw image data for one of the modular segments, including adjacent border portions of the immediately preceding and the next following modular segment and storing the raw image data in a first two-dimensional data array; and processing the digital calibration data and the raw image data into normalized calibration data which are referenced to at least one clearly definable feature that occurs identically in the generated radiographic image of each of the modular segments and storing the normalized calibration data in a calibration data file as a digital template image; and wherein the inspection mode comprises the steps of:
acquiring an acquired radiographic image of a section of the conveyor chain with at least one article travelling on the section, and retaining the acquired radiographic image in the form of raw digital image data in a second two-dimensional data array as a raw digital image of the article with the background of the section of the conveyor chain, arithmetically processing the raw digital image into a normalized digital image which is referenced to the at least one clearly definable feature, and retaining the normalized digital image of the article with the background of the section of the conveyor chain in a two-dimensional data array, and applying a correction to the normalized digital image of the article with the background of the section of the conveyor chain, the correction corresponding to the digital template image, and thereby removing the background of the conveyor chain therefrom.

2. The method of claim 1, wherein:
the radiation source is of a spatially concentrated configuration;
the plurality of photodiodes in the radiation detector comprise a linear array, arranged at regular intervals; and
the radiation source and the radiation detector face each other across the modular conveyor chain, such that the scanning rays emanate from the radiation source as a fan-shaped planar bundle lying in a common scanning plane with the linear array of photodiodes, with the common scanning plane running substantially orthogonal to the travel direction of the conveyor chain.

3. The method of claim 2 wherein:
the step of receiving the scanning rays in the radiation detector comprises triggering the radiation detector in pulses to receive the scanning rays, the pulses being timed to be synchronized with the movement of the conveyor chain, such that the fan-shaped planar bundle of radiation is converted into an output signal of the radiation detector at a uniform travel interval of the conveyor chain and the articles being transported through the scanning plane.

4. The method of claim 2 wherein:
the step of emitting scanning rays comprises the substep of providing from the radiation source a continuous stream of radiation.

5. The method of claim 4, wherein:
the step of converting the received scanning rays comprises the substeps of:
converting the radiation received by the photodiodes at each individual trigger pulse into a line of substantially equidistant image dots;
generating a series of substantially equidistant parallel lines of image dots from a sequence of the individual trigger pulses, so that the lines of image dots form a raw image in the form of a raster of lines and columns of image dots with the following characteristics:
each line of image dots is associated with a trigger pulse occurring at a given point in time;
each column of image dots is associated with a specific photodiode in the linear array of photodiodes;
each image dot in the raster is referenced by a first registration coordinate in terms of raster intervals in the direction perpendicular to the conveyor chain travel direction, and also by a second registration coordinate in terms of raster intervals in the conveyor chain travel direction;
an origin of a two dimension coordinate system defined by the respective first and second registration coordinates is placed at an arbitrarily selected intersection of a raster line and a raster column; and
each image dot is individually characterized by a level of brightness, expressed in digital form as a brightness value.

6. The method of claim 5, wherein:
the brightness value is determined by:
an individually different dark signal and light sensitivity of each photodiode;
an individually different distance of each photodiode from the radiation source;
an individually different amount of radiation intensity lost along a ray path from the radiation source to each photodiode due to absorption in the conveyor chain; and
an individually different amount of radiation intensity lost along the ray path from the radiation source to each photodiode due to absorption in an article under inspection.

7. The method of claim 6, wherein:
the step of measuring the diode current of each of the plurality of photodiodes comprises the substeps of:
turning off the radiation source;
measuring a diode current for each photodiode of the linear array of photodiodes; and
digitizing and storing each measured diode current and storing in a one-dimensional memory array as the dark signal of the diode.

8. The method of claim 6, wherein:
each of the individual modular segments has a substantially flat and relatively thin area with high and substantially uniform transmissibility to the radiation;
the flat area has a substantially rectangular shape that extends extending in an x-direction that is transverse to the travel direction over the entire width of the conveyor chain and that extends, in a y-direction defined by the travel direction, from one hinge to the next;
such that, in the generated radiographic image, the flat areas of the modular segments appear as light areas and the hinges appear as dark stripes, the succession of modular segments forming a pattern of light and dark parallel stripes running transverse to the travel direction of the conveyor chain, the dark parallel stripes providing the clearly definable feature to which the normalized radiographic image data can be referenced.

9. The method of claim 8, wherein:
the step of acquiring raw image data for one of the modular segments comprises the substeps of:
turning on the radiation source on;
setting the conveyor chain in motion;
acquiring raw segment image data for one of the modular segments including the full extent of the two dark stripes representing the immediately preceding and the next following modular segment; and
collecting the raw segment image data in a two-dimensional data array.

10. The method of claim 9, wherein:
the step of processing the digital calibration data and the raw image data into normalized calibration data comprises the substeps of:
  obtaining a net segment image value for each location defined in the two-dimension coordinate system, by subtracting the dark signal from the raw segment image value, the set of net segment image values defining a net segment image data array;
  identifying, in the net segment image data array, the portions that represent the dark stripes, identifying a light area between the dark stripes and calculating a linear calibration array by averaging the net segment image values for each first registration coordinate value within the light area;
  calculating a gain factor that is a function of the reciprocal of the linear calibration array for each first registration coordinate value photodiode, wherein k is a normalization factor;
  multiplying every net segment image value by the gain factor associated with the respective first registration coordinate value to determine an array of normalized segment image values;
  based on the normalized segment image values, calculating within each of the two dark stripes an image-intensity-weighted centroid line within a fraction of a raster interval in the y-direction;
  transforming the normalized segment image values into normalized calibration template values referenced to a normalized coordinate raster, wherein the normalized y-direction coordinate originates from the centroid line and is scaled in terms of the periodic interval between two centroid lines, and wherein the brightness value assigned to each normalized calibration template value is obtained by interpolating between adjacent normalized segment image values; and
  storing the normalized calibration template values in a memory array as the digital template image.

11. The method of claim 10, wherein:
the inspection mode step of acquiring the acquired radiographic image of a section of the conveyor chain with at least one article travelling on the section comprises the substeps of:
  sensing the approach of an article to the scanning plane; and
  acquiring the acquired radiographic image of the articles with the underlying background of the modular conveyor chain in the form of a two-dimension raw image data array.

12. The method of claim 11, wherein:
the inspection mode step of arithmetically processing comprises the substeps of:
  subtracting the dark signals from the raw image data to produce a net image data array;
  multiplying every net image data array value with the gain factor for the corresponding first registration coordinate to obtain a two-dimension array of normalized image values;
  in the normalized image value array, identifying the portions representing the dark stripes and applying the image-intensity-weighted centroid line calculation to those parts of the dark stripes that are not overlapped by the image of an article under inspection; and
  transforming the normalized image value array into a template-referenced image array which is referenced to the coordinate raster of the template image that represents the first full modular segment in the underlying background,
  wherein the brightness value assigned to each raster dot in the template-referenced image array is obtained by interpolating between adjacent normalized image data values.

13. The method of claim 12, wherein:
the inspection mode step of applying a correction to the normalized digital image of the article comprises the substeps of:
  merging the template-referenced image array and the normalized calibration template array in an arithmetic procedure that removes the background of the hinges from the template-referenced digital image, wherein, for each raster location, the respective pixel value in the template-referenced digital image is individually corrected based on the corresponding normalized calibration template value, resulting in a final radiographic image of the article without the background of the modular conveyor chain; and
  analyzing the final radiographic image for the presence of irregularities in the nature of foreign objects that are contained in the article.

14. A system for radiographic inspection of articles, comprising:
  a radiation source that emits scanning rays;
  a radiation detector, comprising an array of photodiodes, for receiving the scanning rays and converting them into detector signals;
  a processor, arranged to receive the detector signals and configured to perform the steps of claim 1, thereby generating a generated radiographic image based on the detector signals; and
  a modular conveyor chain with identical modular segments joined together by hinges, the conveyor chain positioned between the radiation source and the radiation detector to transport the articles under inspection in a travel direction, each of the identical modular segments comprising at least one element which will provide a prominent and clearly defined image feature in the generated radiographic image.

15. The radiographic inspection system of claim 14, wherein:
  each modular segment has a substantially flat and relatively thin area with high and substantially uniform transmissibility to the radiation;
  each flat area being of substantially rectangular shape, extending over the entire width of the conveyor chain in an x-direction transverse to the travel direction and extending in a y-direction in the travel direction from one hinge to the next, such that in the generated radiographic image, the flat areas of the modular segments appear as light areas while the hinges appear as dark stripes, so that in the generated radiographic image the succession of modular segments forms a pattern of light and dark parallel stripes running transverse to the travel direction of the conveyor chain, the dark parallel stripes providing the clearly definable feature to which the normalized radiographic image data can be referenced.

16. The radiographic inspection system of claim 14, wherein:
  the radiation source emits X-rays; and
  the photodiodes, having a maximum spectral sensitivity for radiation with a longer wavelength than X-rays, comprise a fluorescent coating that converts incident X-rays into radiation with a wavelength matched to the maximum spectral sensitivity.

17. The radiographic inspection system of claim 15, wherein:
the radiation source emits X-rays; and
the photodiodes, having a maximum spectral sensitivity for radiation with a longer wavelength than X-rays, comprise a fluorescent coating that converts incident X-rays into radiation with a wavelength matched to the maximum spectral sensitivity.

18. A method for operating a system for radiographic inspection of articles, the method comprising the steps of:
transporting, in a travel direction, an article being inspected on a modular conveyor chain that comprises a plurality of identical modular segments that are joined together by hinges to form a closed loop chain;
emitting scanning rays from a radiation source, the radiation source arranged so that the scanning rays traverse both the article and at least a portion of the modular conveyor chain;
receiving the scanning rays in a radiation detector comprising a plurality of photodiodes;
converting the received scanning rays in the radiation detector into detector signals; and
generating, from the detector signals, a generated radiographic image in a processor, the processor programmed to eliminate, in the generated radiographic image, a background image that is caused essentially by the conveyor chain segments and by factors inherent in the radiation detector, through the use of a calibration mode and an inspection mode,
wherein the calibration mode comprises the steps of:
measuring a diode current of each of the plurality of photodiodes in the following manner:
turning off the radiation source;
measuring a diode current for each photodiode of the plurality of photodiodes; and
digitizing and storing each measured diode current and storing in a one-dimensional memory array as digital calibration data representing the dark signal of the diode,
acquiring raw image data for one of the modular segments, including adjacent border portions of the immediately preceding and the next following modular segment and storing the raw image data in a first two-dimensional data array; and
processing the digital calibration data and the raw image data into normalized calibration data which are referenced to at least one clearly definable feature that occurs identically in the generated radiographic image of each of the modular segments and storing the normalized calibration data in a calibration data file as a digital template image; and
wherein the inspection mode comprises the steps of:
acquiring an acquired radiographic image of a section of the conveyor chain with at least one article travelling on the section, and retaining the acquired radiographic image in the form of raw digital image data in a second two-dimensional data array as a raw digital image of the article with the background of the section of the conveyor chain,
arithmetically processing the raw digital image into a normalized digital image which is referenced to the at least one clearly definable feature, and retaining the normalized digital image of the article with the background of the section of the conveyor chain in a two-dimensional data array, and
applying a correction to the normalized digital image of the article with the background of the section of the conveyor chain, the correction corresponding to the digital template image, and thereby removing the background of the conveyor chain therefrom.

19. A method for operating a system for radiographic inspection of articles, the method comprising the steps of:
transporting, in a travel direction, an article being inspected on a modular conveyor chain that comprises a plurality of identical modular segments that are joined together by hinges to form a closed loop chain;
emitting scanning rays from a radiation source, the radiation source arranged so that the scanning rays traverse both the article and at least a portion of the modular conveyor chain;
receiving the scanning rays in a radiation detector comprising a plurality of photodiodes;
converting the received scanning rays in the radiation detector into detector signals; and
generating, from the detector signals, a generated radiographic image in a processor, the processor programmed to eliminate, in the generated radiographic image, a background image that is caused essentially by the conveyor chain segments and by factors inherent in the radiation detector, through the use of a calibration mode and an inspection mode,
wherein the calibration mode comprises the steps of:
measuring a diode current of each of the plurality of photodiodes while the radiation source is turned off and storing the measured diode currents as digital calibration data in a one-dimensional data array,
acquiring raw image data for one of the modular segments, including adjacent border portions of the immediately preceding and the next following modular segment and storing the raw image data in a first two-dimensional data array; and
processing the digital calibration data and the raw image data into normalized calibration data which are referenced to at least one clearly definable feature that occurs identically in the generated radiographic image of each of the modular segments and storing the normalized calibration data in a calibration data file as a digital template image; and
wherein the inspection mode comprises the steps of:
acquiring an acquired radiographic image of a section of the conveyor chain with at least one article travelling on the section by the substeps of:
sensing the approach of an article to a scanning plane;
acquiring the generated radiographic image of the articles with the underlying background of the modular conveyor chain in the form of a two-dimension raw image data array; and
retaining the generated radiographic image in the form of raw digital image data in a second two-dimensional data array as a raw digital image of the article with the background of the section of the conveyor chain;
arithmetically processing the raw digital image into a normalized digital image which is referenced to the at least one clearly definable feature, and retaining the normalized digital image of the article with the background of the section of the conveyor chain in a two-dimensional data array, and
applying a correction to the normalized digital image of the article with the background of the section of the conveyor chain, the correction corresponding to the digital template image, and thereby removing the background of the conveyor chain therefrom.

* * * * *

UNITED STATES PATENT AND TRADEMARK OFFICE
CERTIFICATE OF CORRECTION

PATENT NO. : 9,727,961 B2  
APPLICATION NO. : 14/310010  
DATED : August 8, 2017  
INVENTOR(S) : Wang et al.

Page 1 of 1

It is certified that error appears in the above-identified patent and that said Letters Patent is hereby corrected as shown below:

In the Claims

In Column 15, Line 18, please delete the word "photodiode".

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*